United States Patent
Di Palma et al.

(10) Patent No.: US 10,987,039 B2
(45) Date of Patent: Apr. 27, 2021

(54) MICRONEEDLE ARRAY DEVICE AND METHOD OF MAKING

(71) Applicant: STMicroelectronics S.r.l., Agrate Brianza (IT)

(72) Inventors: Vincenza Di Palma, Cimitile (IT); Maria Fortuna Bevilacqua, Gragnano (IT); Andrea Di Matteo, Naples (IT); Principia Dardano, Ercolano (IT)

(73) Assignee: STMICROELECTRONICS S.R.L., Agrate Brianza (IT)

(*) Notice: Subject to any disclaimer, the term of this patent is extended or adjusted under 35 U.S.C. 154(b) by 530 days.

(21) Appl. No.: 14/558,779

(22) Filed: Dec. 3, 2014

(65) Prior Publication Data

US 2016/0157764 A1    Jun. 9, 2016

(51) Int. Cl.
*A61B 5/1486* (2006.01)
*A61B 5/145* (2006.01)
*A61B 5/00* (2006.01)

(52) U.S. Cl.
CPC ...... *A61B 5/14865* (2013.01); *A61B 5/14514* (2013.01); *A61B 5/14532* (2013.01); *A61B 5/1486* (2013.01); *A61B 5/14546* (2013.01); *A61B 5/685* (2013.01); *A61B 2562/046* (2013.01)

(58) Field of Classification Search
CPC ............ A61B 5/14532; A61B 5/14514; A61B 5/14865; A61B 5/1486; A61B 5/685; A61B 2562/046
See application file for complete search history.

(56) References Cited

U.S. PATENT DOCUMENTS

| | | | |
|---|---|---|---|
| 6,162,611 A | 12/2000 | Heller et al. | |
| 6,221,238 B1 | 4/2001 | Grundig et al. | |
| 6,485,703 B1* | 11/2002 | Cote | A61K 49/0041 424/9.1 |
| 7,344,499 B1* | 3/2008 | Prausnitz | A61M 37/0015 600/309 |
| 7,943,089 B2 | 5/2011 | Yang et al. | |
| 2001/0003045 A1 | 6/2001 | Davis et al. | |
| 2002/0082543 A1 | 6/2002 | Park et al. | |
| 2002/0188221 A1 | 12/2002 | Sohrab | |
| 2003/0106809 A1 | 6/2003 | Kermani et al. | |
| 2004/0096959 A1 | 5/2004 | Stiene et al. | |
| 2005/0075572 A1* | 4/2005 | Mills | B06B 1/0292 600/459 |

(Continued)

OTHER PUBLICATIONS

Yan et al., "Immobilizing Enzymes Onto Electrode Arrays by Hydrogel Photolithography to Fabricate Multi-Analyte Electromechanical Biosensors," Applied Materials & Interfaces, vol. 2, No. 3, Feb. 16, 2010; pp. 748-755.

(Continued)

*Primary Examiner* — Christian Jang
*Assistant Examiner* — Karen E Toth
(74) *Attorney, Agent, or Firm* — Slater Matsil, LLP

(57) ABSTRACT

A microneedle array device includes a substrate and an array of microneedles on the substrate. Each microneedle includes a redox enzyme and redox mediator and an electrically conductive layer on the substrate. The electrically conductive layer may extend partway up each microneedle exposing the tip thereof.

24 Claims, 10 Drawing Sheets

(56) References Cited

U.S. PATENT DOCUMENTS

| | | | |
|---|---|---|---|
| 2006/0094946 A1* | 5/2006 | Kellogg | A61B 5/14514 600/347 |
| 2006/0264716 A1* | 11/2006 | Zander | A61B 5/14532 600/309 |
| 2009/0131905 A1* | 5/2009 | Allen | A61B 5/14514 604/501 |
| 2010/0256064 A1* | 10/2010 | Woolfson | A61B 17/205 514/15.2 |
| 2010/0292551 A1 | 11/2010 | Jina | |
| 2013/0004649 A1 | 1/2013 | Bommakanti et al. | |
| 2014/0017772 A1 | 1/2014 | Di Matteo et al. | |
| 2014/0336487 A1* | 11/2014 | Wang | A61D 5/685 600/352 |

OTHER PUBLICATIONS

Slaughter, "Fabrication of Nanoindented Electrodes for Glucose Detection," Journal of Diabetes Science and Technology, vol. 4, Issue 2, Mar. 2010; pp. 320-327.

Kochhar et al., "A Simple Method of Microneedle Array Fabrication for Transdermal Drug Delivery," Drug Development and Industrial Pharmacy, 2013; 39(2); pp. 299-309.

\* cited by examiner

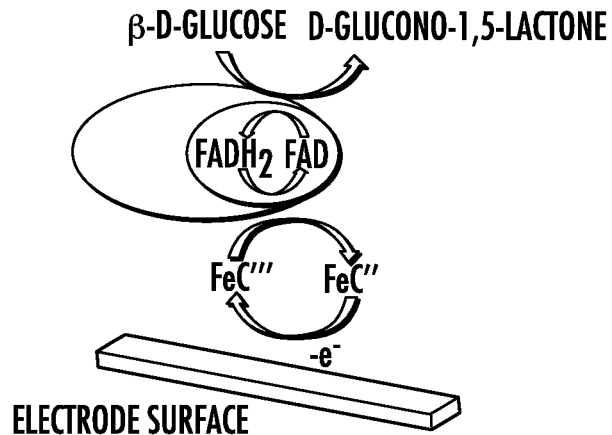
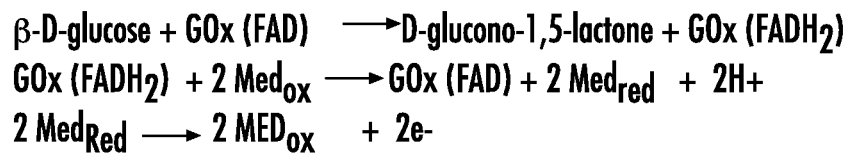
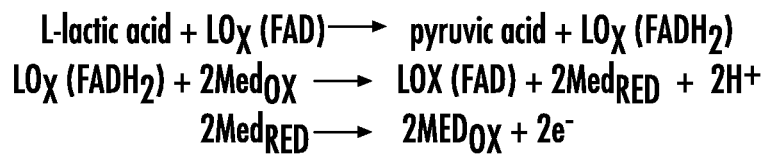
FIG. 6

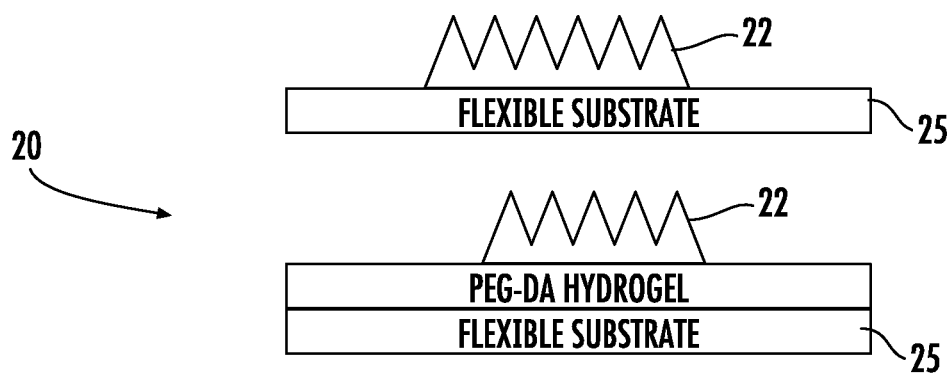
FIG. 9A
FIG. 9B
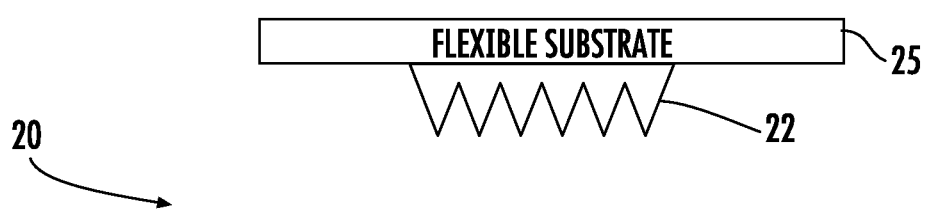
FIG. 10A
FIG. 10B

US 10,987,039 B2

MICRONEEDLE ARRAY DEVICE AND METHOD OF MAKING

FIELD OF THE INVENTION

The present invention relates to the field of microneedle array devices, and more particularly, to microneedle array devices used as biosensors to detect a bioanalyte such as glucose or Lactate and the like.

BACKGROUND OF THE INVENTION

There is a need for the continuous monitoring in humans and other animals of bioanalytes such as glucose and lactate. There are many commercially available non-invasive devices formed as electro-chemical sensors known also as biosensors. Most of these commercially available devices, however, are not discrete and painless. Many different biosensors are available to detect a bioanalyte, such as glucose and lactate, and usually include a bio-recognition element formed as a sensitive biological sensing element, and a transducer element that transforms a signal resulting from the interaction of the analyte with the biological sensing element into another signal that can be more easily measured and quantified. In one example, the bio-recognition element is formed as an antibody or enzyme attached to a sensitive surface forming the sensing part of the biosensor. The recognition may occur through a redox process between the enzyme and analyte providing a transfer of electrons to an electrode (transductor part of the biosensor). Some devices operate using a redox mediator to facilitate electron transfer with an analyte and redox enzyme. One drawback to using these conventional bio-recognition elements is that they may easily denature and lose their activity. Also, the elements must be immobilized, which can be obtained by chemical cross-linking, electro deposition, electrostatic interactions, or entrapment within solid polymer membranes such as hydrogel matrices and the like.

Hydrogels are attractive for immobilizing electro-chemical detectors because they provide near physiological conditions that minimize protein denaturation and help carry out full biological functions. Hydrogels have three-dimensional porous matrices and may contain a large quantity of the sensing element, increasing their signal-to-noise ratio and sensitivity. Use of photo cross-linking (photo definable) hydrogel polymers have opened new techniques to develop new hydrogel photoresists that help develop photodefined biocompatible matrices for encapsulation of bio-recognition enzymes. Immobilization can occur by cross-linking where the enzyme is physically/chemically entrapped within the bulk of the polymer or in the mesh of a swollen polymer network.

It is also possible to form a membrane with a specific property through photo cross-linking of a suitable polymer that can be accomplished via photo-reactive side groups of the polymer or via addition of a photo-sensitizer or photo-initiator into the polymer solution or gel. An example is disclosed in commonly assigned U.S. Patent Publication No. 2014/0017772, the disclosure which is hereby incorporated by reference in its entirety.

Further improvements in biosensors that use redox mechanisms are desirable and would be advantageous in order to ensure analyte monitoring in the interstitial tissue with reduced pain and a smaller amount of space on the body with the fast response.

SUMMARY OF THE INVENTION

A microneedle array device includes a substrate and an array of microneedles on the substrate. Each microneedle includes a redox enzyme and redox mediator and an electrically conductive layer on the substrate. The electrically conductive layer may extend partway up each microneedle exposing the tip thereof.

In one example, each microneedle is formed from a biocompatible hydrogel, which in an example comprises polyethylene glycol diacrylate having a molecular weight between 200 to 6000 daltons. In another example, the redox enzyme includes at least one of glucose oxidase and lactate oxidase. The redox mediator may be formed from vinylferrocene. The redox mediator shifts between oxidized and reduced states and facilitates electron transfer during a reaction between an analyte and the redox enzyme in a physiological medium. In another example, the analyte is formed from at least one of glucose and lactate. A controller may be coupled to the array of microneedles.

A method of making a microneedle array device includes forming an array of microneedles on a substrate with each microneedle comprising a redox enzyme and redox mediator and forming an electrically conductive layer on the substrate, as example a gold or gold/titanium layer. This electrically conductive layer may be formed to extend partway up each microneedle exposing the tip thereof.

BRIEF DESCRIPTION OF THE DRAWINGS

FIG. 6 is a drawing representation of the electron shuttling using the redox mediator and enzyme/analyte reaction on the electrode surface for Glucose and Lactate analytes.

FIGS. 9A and 9B show abstract sectional drawings for the first flow diagram of FIG. 7.

FIGS. 10A and 10B show abstract sectional drawings for the flow diagram of FIG. 8.

DETAILED DESCRIPTION OF THE
PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
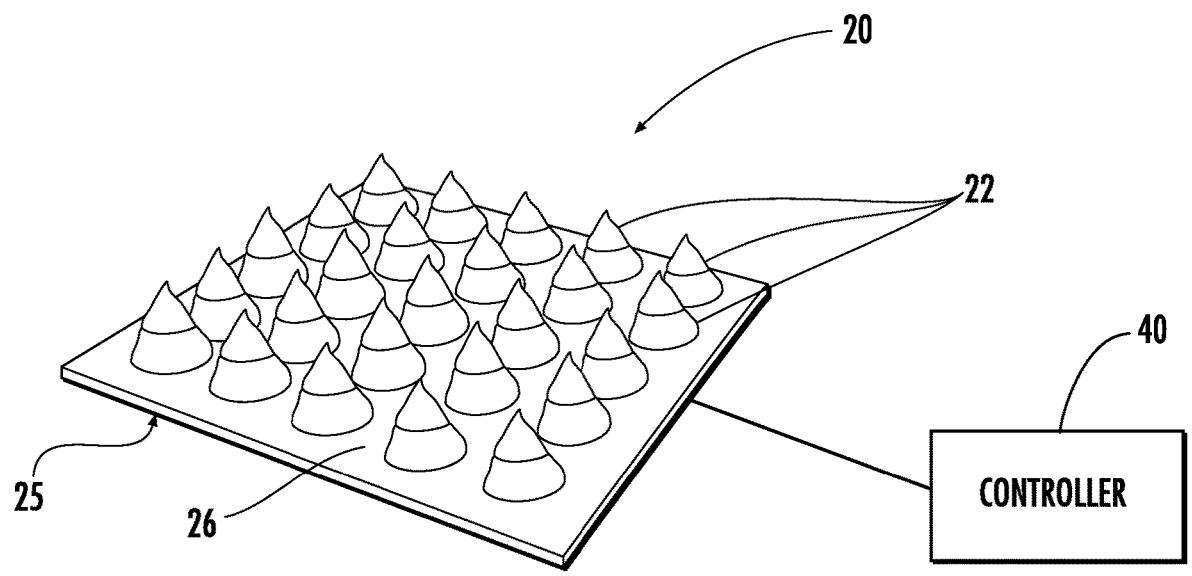
FIG. 1 is a perspective view of the microneedle array device and showing the array of microneedles on a substrate and a controller coupled to the array of microneedles in accordance with a non-limiting example.

FIG. 1 shows a microneedle array device 20 in accordance with a non-limiting example that operates as an electrochemical biosensing device based on an array of biocompatible microneedles 22 formed from a hydrogel 24 that is non-toxic to living tissue. The hydrogel photo-definable is made of water swollen hydrophilic materials that consist of polymeric chains that are crosslinked together either covalently or not covalently. Their monomers or prepolymers are soluble in water, while the polymers are insoluble in water at physiological temperature, pH value and ionic strength. They will swell to an equilibrium value of 10% to 98% $H_2O$ physiologic temperature, pH value and ionic strength. The water content (% $H_2O$) is defined as % $H_2O=100\times$(weight swollen polymer-weight dry polymer)/weight swollen polymer. The polymers may have a molecular weights in the range 500-200000 dalton whose properties, including viscosity, softening temperature and degradation temperature, are optimized according to the specific application.

The hydrogel photo-definable membrane for this application may be composed of a monomer, oligomer or prepolymers (the molecular weight of prepolymer controls mechanical properties and viscosity), or binder which ensure mechanical properties of the mixture (adhesion, chemical strength etc); of a solvent which controls a number of the mechanical properties (for example the viscosity of the mixture); and of photo-active materials (PAC) or photoinitiators (Phi). The composition of hydrogel used for this application must guarantee the indentation in human tissue in terms of ratio of components and the mixture thereof.

The hydrogel photo definable membrane behaves like a negative photoresist used in negative photolithographic process, where a water development removes the photoresist portion that was not exposed to irradiation. In this case, the hydrogel photo-definable membrane material containing the precursor monomers or oligomer or prepolymer for exposure to the incident UV radiation, for example, undergoes photo-polymerization and/or photo cross linking reaction. The cross-linking of membrane determines an increase of its molecular weight, which induces an advantageous diminution of solubility of the membrane in water.

Examples of hydrogel photo-definable membranes composed of simple monomers or a mix of different monomers are:

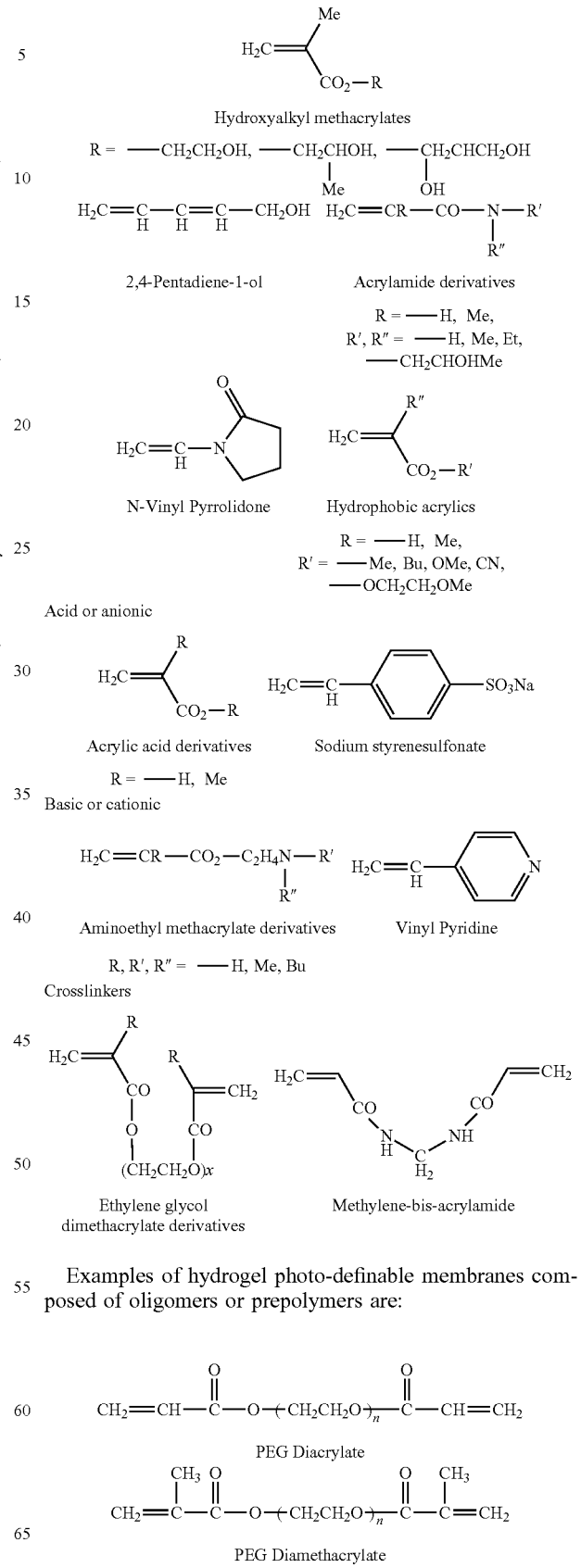

Examples of hydrogel photo-definable membranes composed of oligomers or prepolymers are:

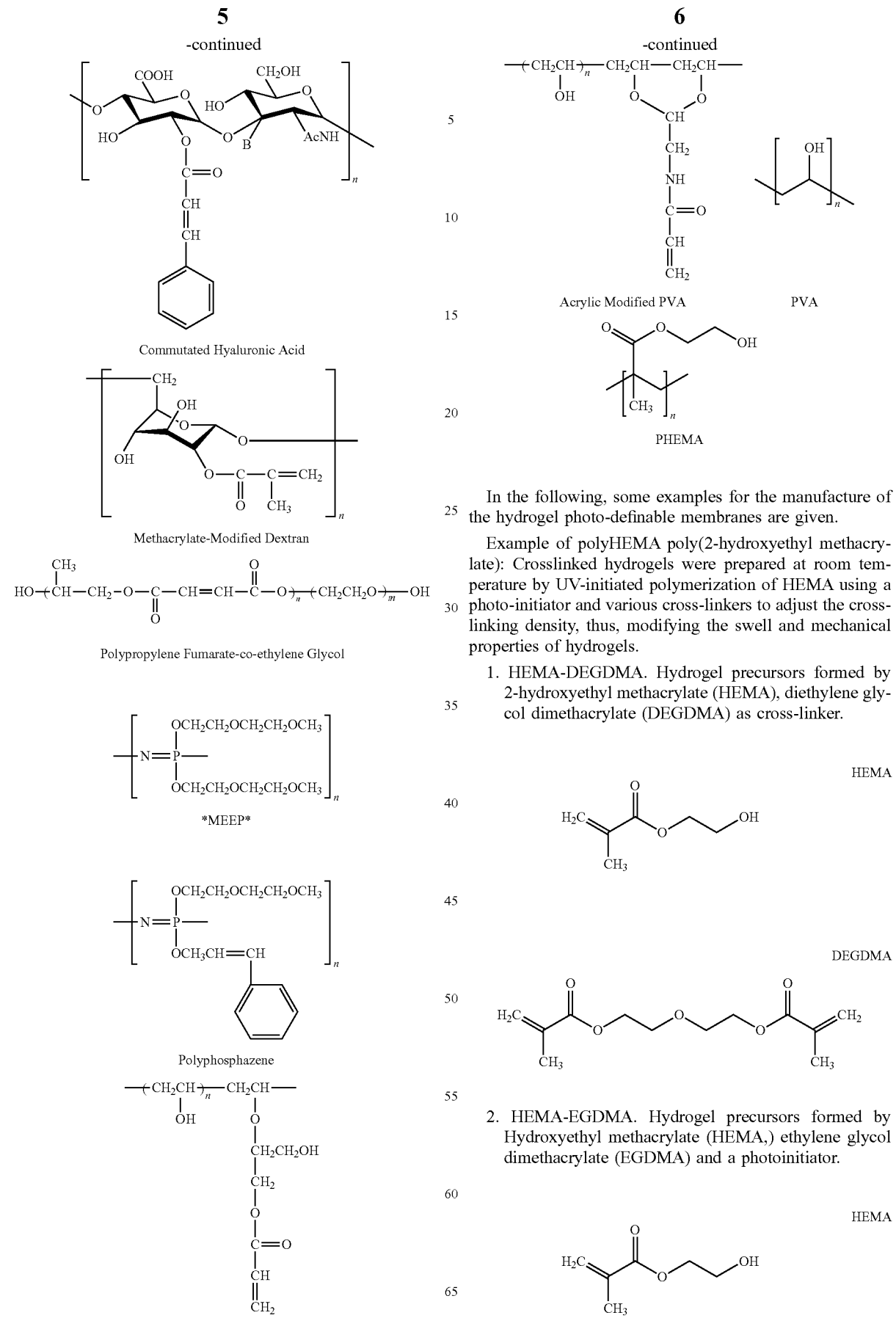

In the following, some examples for the manufacture of the hydrogel photo-definable membranes are given.

Example of polyHEMA poly(2-hydroxyethyl methacrylate): Crosslinked hydrogels were prepared at room temperature by UV-initiated polymerization of HEMA using a photo-initiator and various cross-linkers to adjust the cross-linking density, thus, modifying the swell and mechanical properties of hydrogels.

1. HEMA-DEGDMA. Hydrogel precursors formed by 2-hydroxyethyl methacrylate (HEMA), diethylene glycol dimethacrylate (DEGDMA) as cross-linker.

2. HEMA-EGDMA. Hydrogel precursors formed by Hydroxyethyl methacrylate (HEMA,) ethylene glycol dimethacrylate (EGDMA) and a photoinitiator.

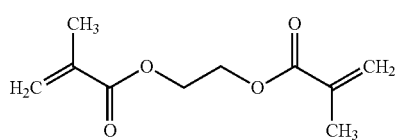

EGDMA

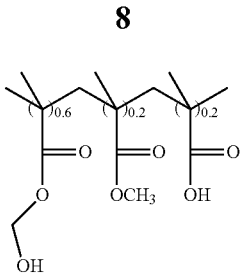

3. PHEMA-co-PMMA Hydrogel precursors formed by poly(2-hydroxyethyl methacrylate-co-methyl methacrylate PHEMA-co-PMMA, photoacid generators and external crosslinkers tetramethoxymethyl glycoluril (TMMGU).

5. PHEMA-PPy. The polymer mixture was formed by hydroxyethylmethacrylate (HEMA), the crosslinker

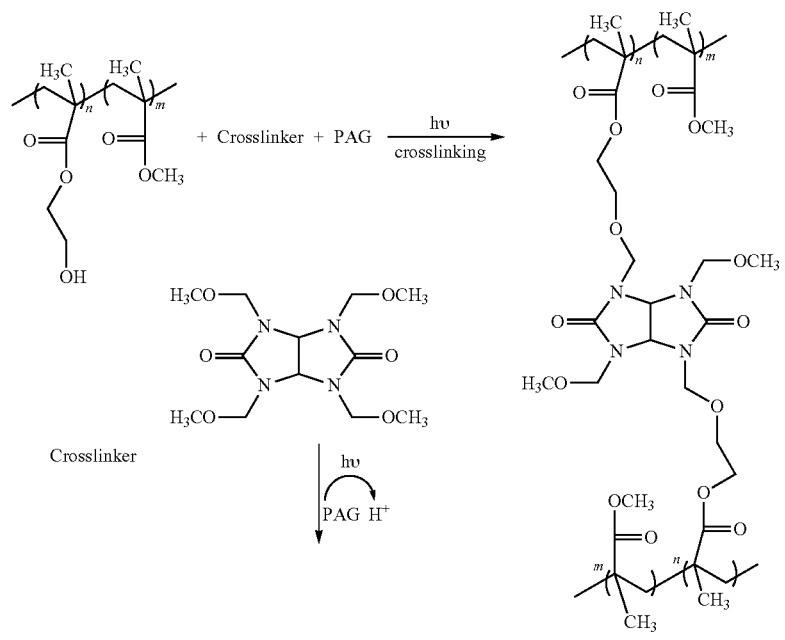

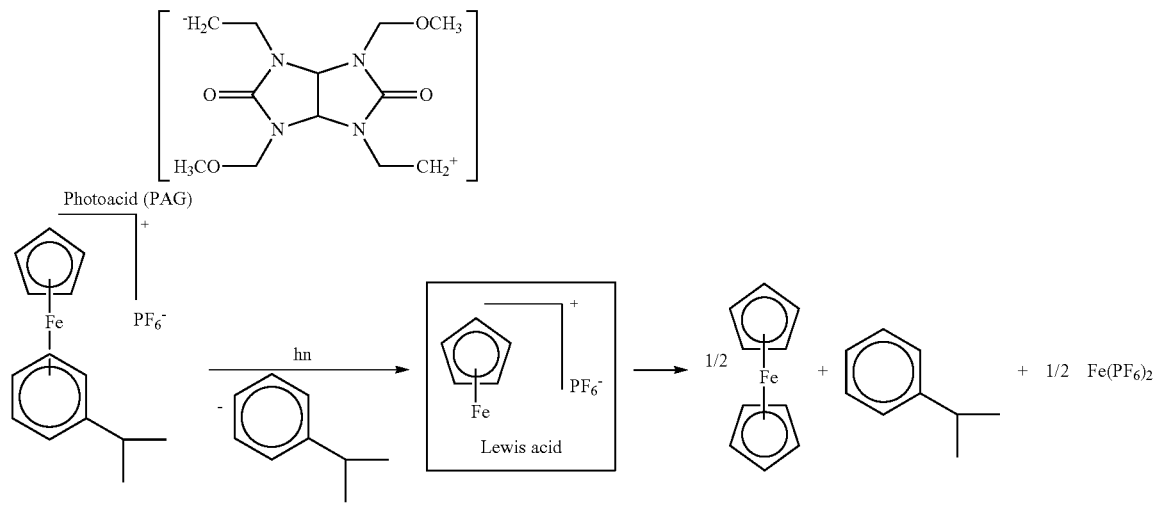

4. poly(HEMA-r-MMA-r-MAA): Poly(Hydroxyethyl methacrylate-r-Methylmethacrylate-r-Methacrylic Acid). MAA is incorporated in order to make the polymer responsive to various pH conditions which can be used to make a smart drug-delivery system.

etraethyleneglycol diacrylate (TEGDA), the photoinitiator dimethoxyphenyl acetophenone (RMPA), pyrrole monomer and the enzyme.

6. HEMA-DHPMA with VP. Copolymer of hydroxyethyl methacrylate (HEMA) and 2,3-dihydroxypropyl methacrylate (DHPMA). The porosity and mechanical properties of the hydrogels were improved using N-vinyl-2-pyrrolidinone (VP) as structural strengthener and ethyleneglycol dimethacrylate (EGDMA) as crosslinker.

Methacrylated Derivitized Polymers:

1. Met-HA. Methacrylate derivatized hyaluronic acid.

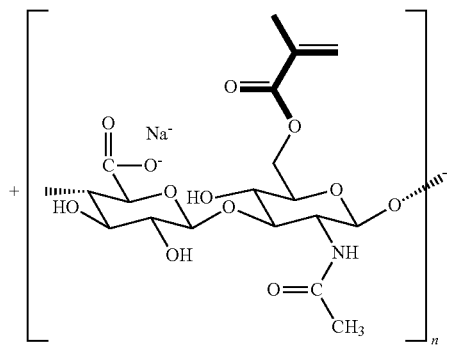

2. Met-PG. Methacrylated hyperbranched polyglycerol

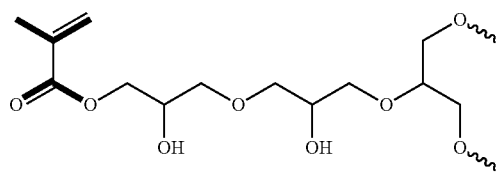

Example of Polyvinyl Alcohol PVA-Based Hydrogel

1. Photoactive PVA. A water based solution of PVA with ammonium dichromate is a negative photoresist.

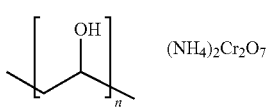

2. Acrylated-PVA. Aqueous solutions of PVA modified by reaction with methacrylamido-acetaldehyde dimethyl acetal to derivatize the PVA with crosslinkable side groups.

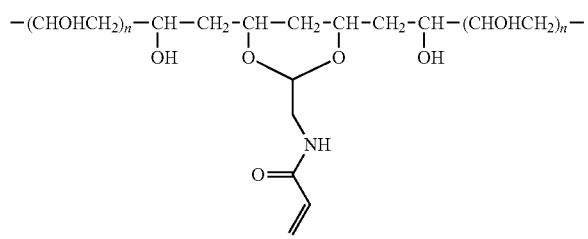

3. PPy-PVA. PVA films exposed to a solution of Pyrrol.

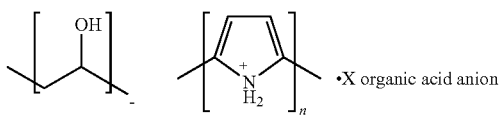

Example of Poly(ethylene glycol) PEG

Polyethylene glycol, with its hydroxyl moieties can be acrylated to polyethylene glycol diacrylate (PEG-DA) or polyethylene glycol methyl diacrylate. Acrylate monomers are esters containing vinyl groups directly bonded to the carbonyl atom. A mixture of PEG-DA, with an appropriate molecular weight, and photoinitiator (e.g., Darocure 1173) under UV exposure forms an insoluble three dimensional polymer network, hydrogel membrane. In particular, the photoinitiator generate a photofragment that start the polymerization, by attaching the double cc bond in the acrylate moieties.

Copolymerization of multiple different hydrogel precursors, either by use of co-polymers in the precursor itself or by random co-polymerization during lithographic process, provides an additional degree of flexibility in the choice of the appropriate hydrogel membrane photo-definable.

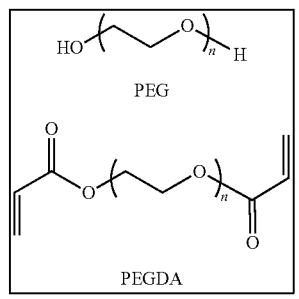

Polyphosphazenes

Polyphosphazenes represent a highly tailorable class of polymers that possess a phosphorus-nitrogen backbone. Several water-soluble polyphosphazenes have been prepared that can be covalently or conically cross-linked to form hydrogels.

The utility of polyphosphazene hydrogels as platforms for enzyme and cell immobilization on a macroscale has also been demonstrated. In particular, polyphosphazenes with alkyl ether and cinnamyl side groups for hydrogel formation via UV photolithography are investigated for enzyme immobilization in use in a range of microscale enzyme based biosensors.

1. MEEP. A poly[bis(methoxyethoxyethoxy)phosphazene] solutions.

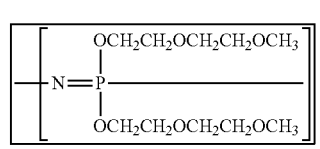

2. Polyphosphazenes with cinnamyl side groups.

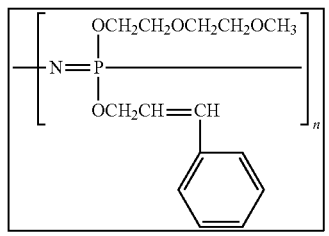

Figure 2:
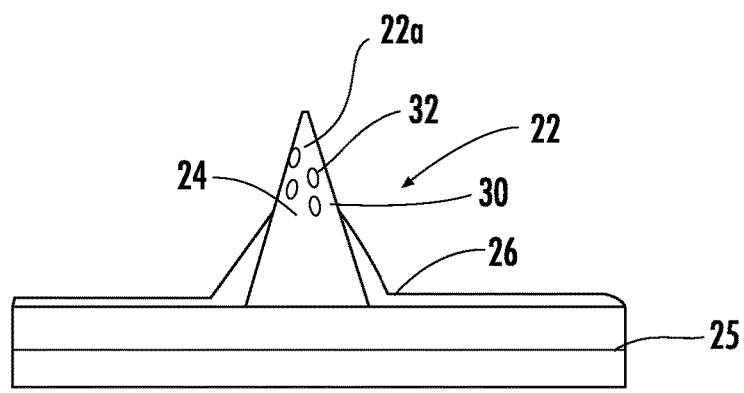
FIG. 2 is a sectional view of one of the microneedles on the substrate in accordance with a non-limiting example.

The microneedles can be arranged as a patch on a substrate 25 to provide the minimum amount of space when placed on the body, ensure a fast response, and implement the possibility of multianalyte monitoring in the interstitial tissue with reduced pain. Each microneedle 22 acts as a microdevice to record the analyte concentration. Each microneedle 22 may be formed from a biocompatible and photodefinable hydrogel 24 (FIG. 2) that includes an electrically conductive layer 26 on the substrate 25 with the layer 26 extending partway up each microneedle 22 and exposing the tip 22a thereof as best shown in FIG. 2. Each microneedle 22 is connected with others by the continuous electrically conductive layer 26 on the substrate 25 formed in one example as a gold metal film. Other conductive materials may be used. The microneedle 22 includes a redox enzyme 30 and redox mediator 32 contained within the hydrogel 24. The microneedles carry out a redox reaction in the presence of a specific analyte, such as glucose, providing an electrical current proportional to the analyte amount in the physiological medium, such as blood or interstitial liquid.

In another example, the substrate may be formed from a flexible polymeric foil such as PET(polyethylene terephthalate), PEH (polyethylene terephthalate), PEN (polyethylene naphthalate), PEEK (polyether ether ketone), PI (polyimide), silicones and siloxanes.

In one example, the biocompatible hydrogel 24 is formed from polyethylene glycol diacrylate that has a molecular weight between about 200 to 6,000 Daltons, and in one example, 250 Daltons. The redox enzyme 30 may be formed from at least one of glucose oxidase and lactate oxidase and the redox mediator 32 in an example is formed from vinylferrocene. Mediators according to this application may be ferrocene derivatives, ferricyanide, conducting organic salts (particularly tetrathiafulvalene-tetracyanoquinodimethane, TTF-TCNQ), quinone compounds, transition-metal complexes, and phenothiazine and phenoxazine compounds, and osmium bipyridine complexes. The analyte can be one of at least glucose and lactate.

A controller 40 is coupled to the array of microneedles 22. Each microneedle is connected with other microneedles by the continuous conductive layer forming the array so that the microneedles are addressed by the external electronic control. The redox mediator 32 as vinylferrocene in this example shuttles electrons from the enzyme/analyte reaction of glucose oxidase, such as from *pergillus niger*/D-glucose or lactate oxidase from *pediococcus*/lactic acid, through the hydrogel 24 (PEG-DA) to the electrode 26 that extends partway up each microneedle exposing the tip thereof.

Figure 3:
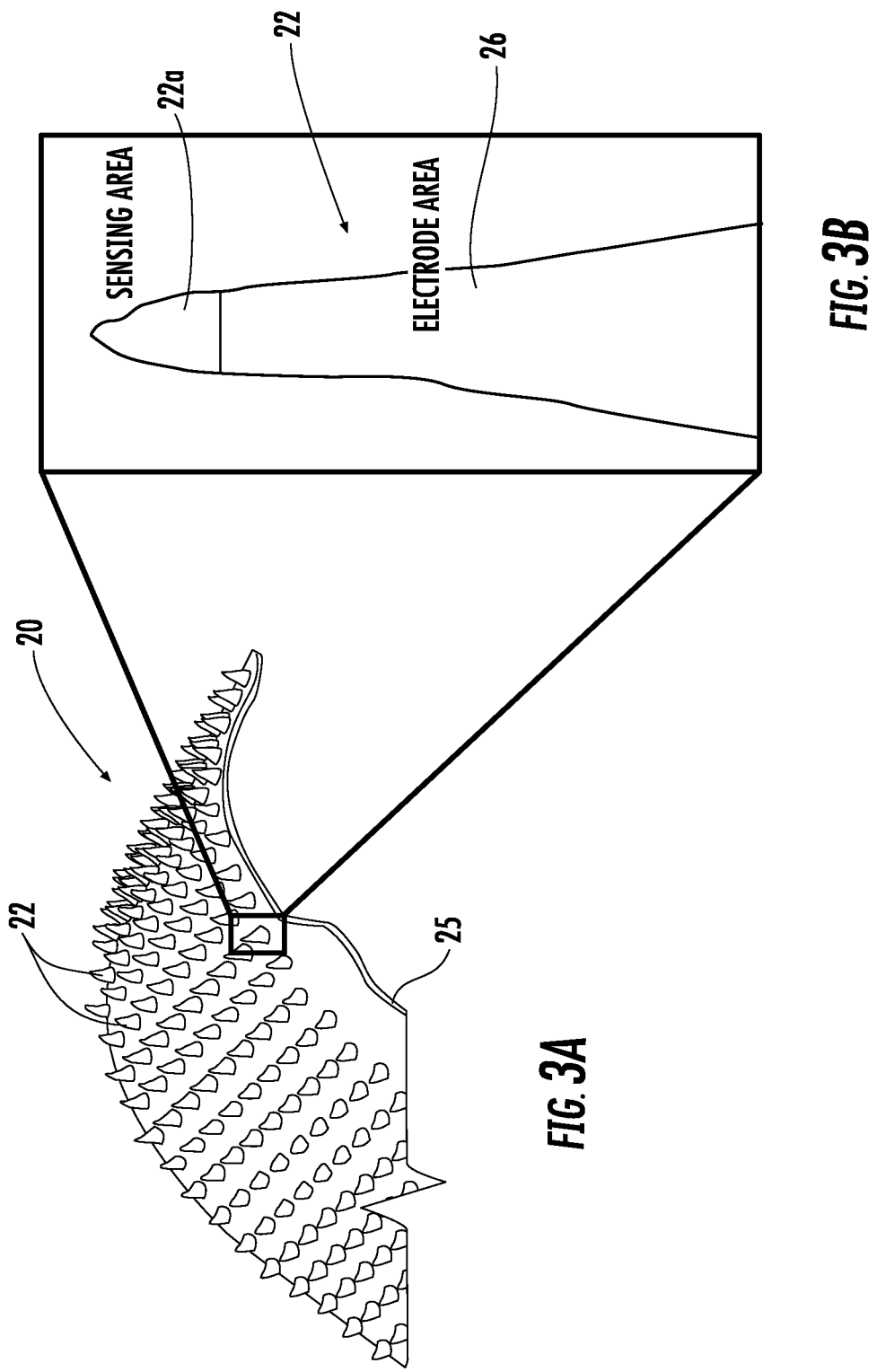
FIG. 3A is a perspective view of the microneedle array device formed on a flexible substrate in accordance with a non-limiting example.
FIG. 3B is an enlarged view of a microneedle showing a sensing area formed by the exposed tip and an electrode area formed by an electrically conductive layer extending partway up the microneedle in accordance with a non-limiting example.

FIG. 3A shows the microneedle array device 20 that includes the flexible substrate 25 that can be formed from different materials as known to those skilled in the art. In one example, it is formed from a flexible foil with the electrode layer 26 formed by the electrically conductive layer on the substrate 25. FIG. 3B shows an enlarged view of one microneedle 22 showing an electrode area 26 formed by the electrically conductive layer and the sensing area formed by the exposed tip 22a.

Figure 4:
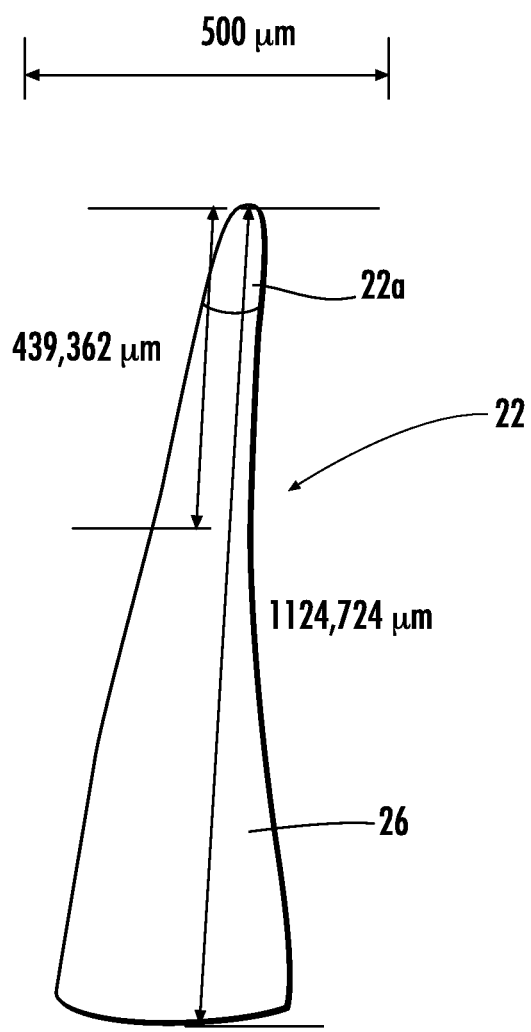
FIG. 4 is an enlarged perspective view of a microneedle showing the relative distances for the height of the microneedle and the electrically conductive layer that extends partway up each microneedle and the exposed tip in accordance with a non-limiting example.

FIG. 4 shows an example microneedle 22 that has a total height of 1124.724 um with the exposed tip 22a having a height of 439.362 um. The electrically conductive layer extends partway up each microneedle and exposes the tip thereof as shown in FIG. 4. In an example, it may extend from as low as 30% to as much as 90% of the height. In another example, it is from 40-90% and in another, about 50-80% and in yet another, about 60%. These values can vary of course depending on end user requirements and design and manufacturing constraints.

Figure 5:
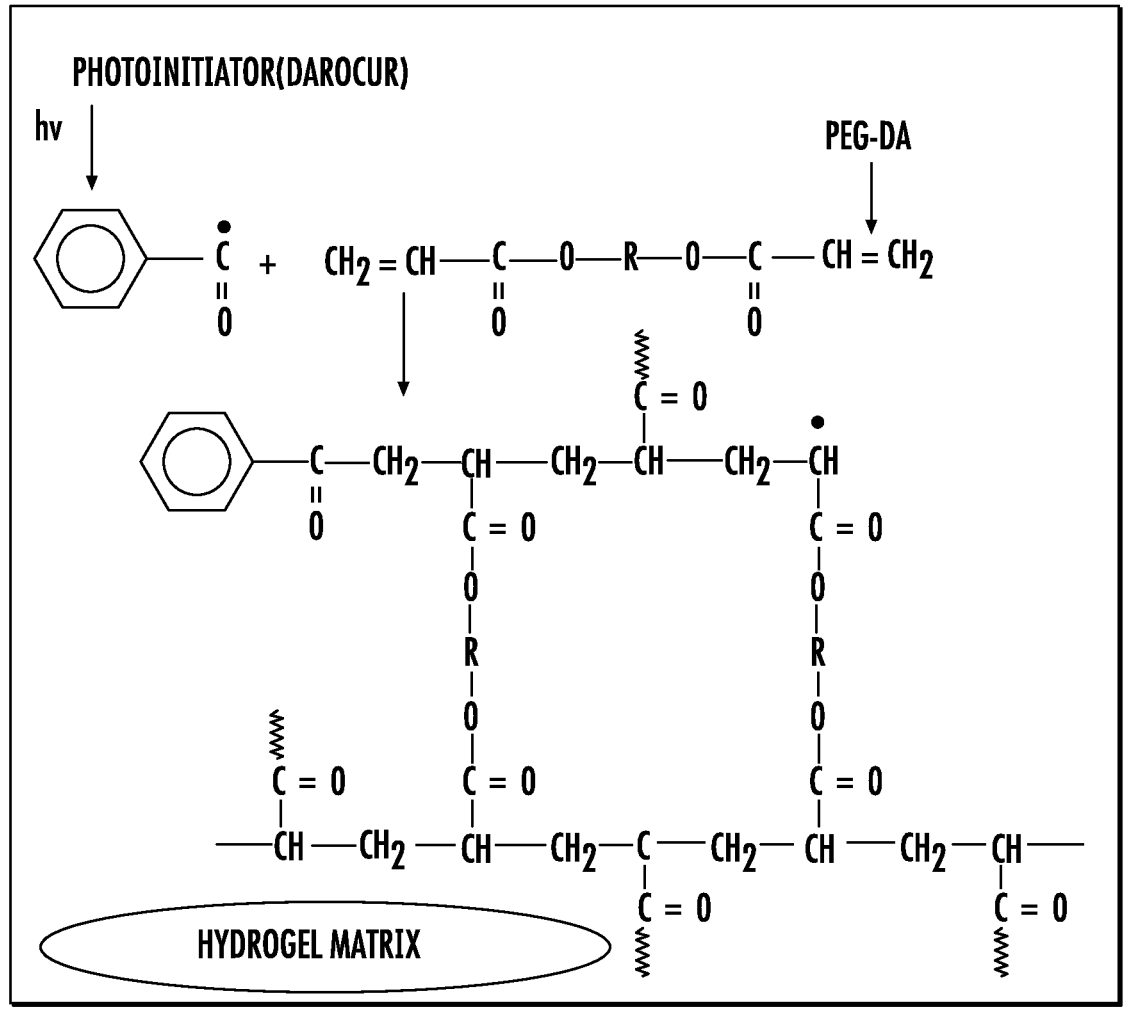
FIG. 5 is a structural formula of the hydrogel as possible matrix for the sensing part of microneedle and showing the photo-initiator as Darocur that initiates the curing to form the hydrogel matrix.

FIG. 5 is a structural chemical formula showing the hydrogel matrix where a photo initiator (Darocur) initiates curing. In one example, the photo initiator is 2-hydroxy-2-methyl-propiophenone. FIG. 6 is an abstract drawing of how the redox mediator of vinylferrocene will shuttle electrons using the electrode surface. The specific chemical reaction for glucose and for lactase is shown in FIG. 6.

In the example above, the biocompatible hydrogel is formed from polyethylene glycol diacrylate and has a molecular weight of between 200 to 6,000 Daltons. Other hydrogel photodefinable membranes may be used such as disclosed in the incorporated by reference and commonly assigned '772 patent publication.

Referring now to FIGS. 7-12, there are shown a series of flow diagrams for the different sequences used to form the microneedle array device 20 in accordance with a non-limiting example. An adhesive layer based on an organosilane solution is deposited on a flexible substrate 25. The silane acts as a coupling agent for the further step of hydrogel sensitive matrix deposition that ensures covalent anchoring of the hydrogel on the flexible substrate. In one example, the silane agent is 3-(trimethoxysilyl) propyl methacrylate that is dissolved in a hydro-alcoholic solution and deposited on a flexible foil as the substrate. This silane layer is heated until a covalent bond is formed between the substrate and silane. The deposition steps include the $O_2$ plasma treatment of the flexible foil with the electrode and the preparation of a solution for silane deposition with hydrolysis and condensation of silane-oligomers. The flexible foil as the substrate is immersed in the silane solution and rinsed in a solvent with the formation of the substrate-silane bond at high temperatures.

Figure 7:
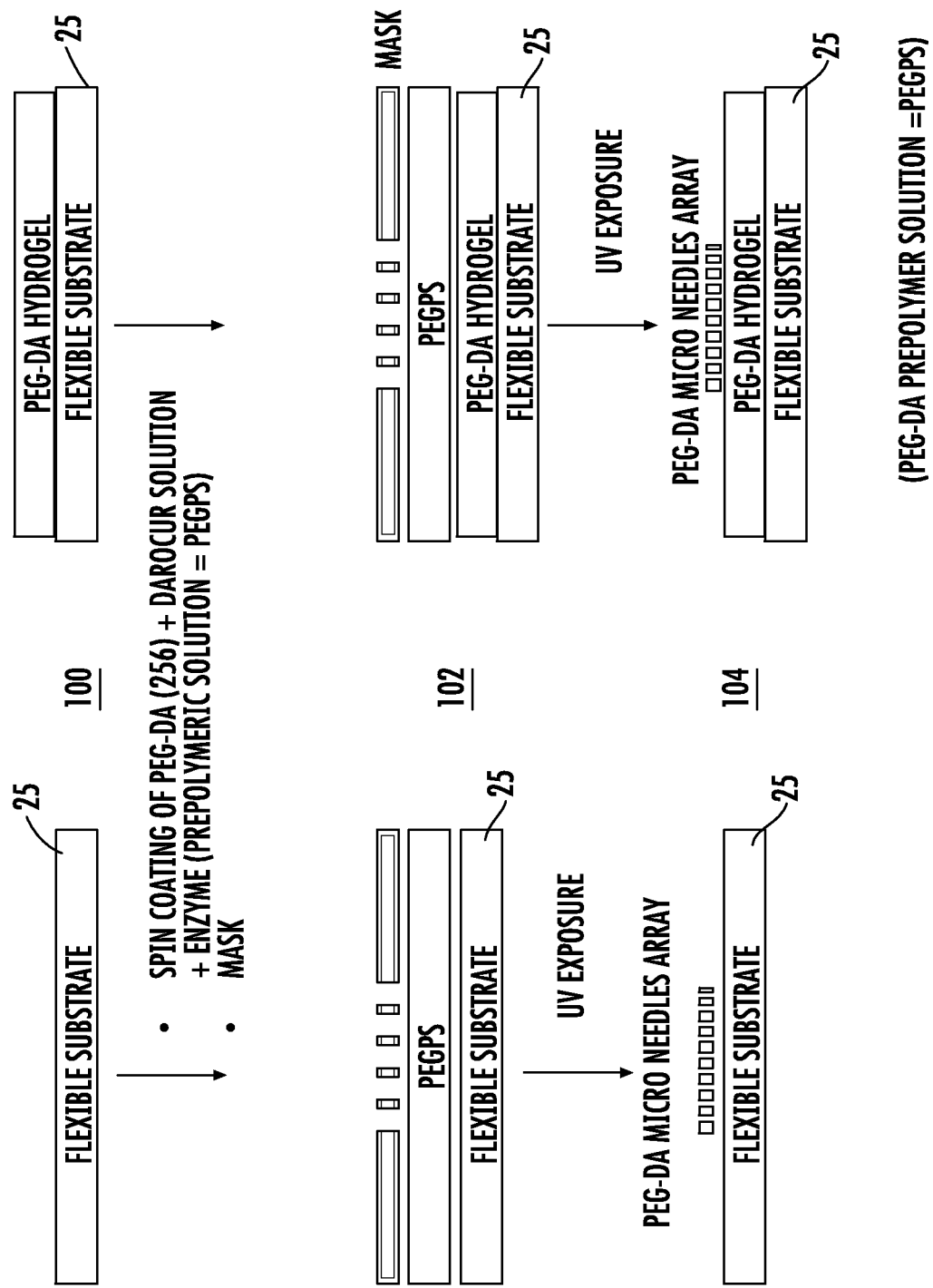
FIG. 7 is a flow diagram showing a first route to form the microneedle array device.

FIG. 7 shows a first flow sequence in which the PEG DA hydrogel formed as the polyethylene glycol diacrylate is photo-patterned in the shape of a microneedle. The hydrogel is charged with an enzyme, such as the glucose oxydase or lactate oxidase, and a redox mediator, such as vinylferrocene, to record a change of current in the presence of analyte, such as glucose and lactate in the body. This deposition is carried out as shown in FIG. 7 with spin coating of the PEG DA 100 plus a Darocur solution, plus the enzyme as a pre-polymeric solution corresponding to the PEGPS in the flow sequence. This is poured in a silicon wall and the flexible substrate is placed bottom up on the wall and a mask is placed on the substrate 102. An array of microneedles is photo-patterned under ultraviolet (UV) radiation 1434. The hydrogel as charged acts as a negative resist. Development occurs in water to remove the UV unexposed membrane.

FIGS. 9A and 9B show the flexible substrate that supports the array of microneedles and shows the PEG-DA hydrogel layer. FIG. 9A corresponds to the left side flow sequence of FIG. 7 and FIG. 9B corresponds to the right side flow sequence of FIG. 7.

Figure 8:
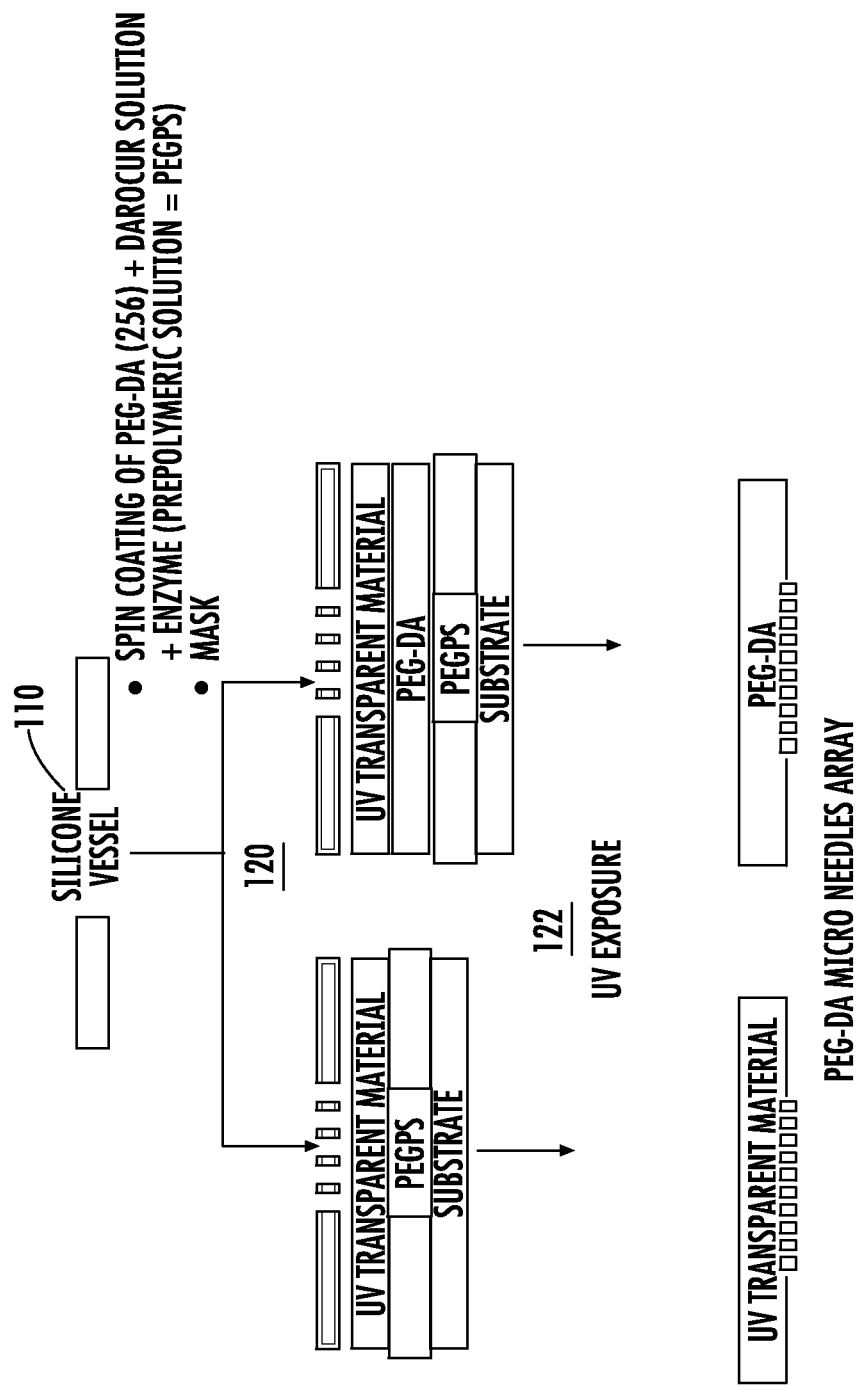
FIG. 8 is a flow diagram showing a second route to form the microneedle array device.

FIG. 8 is an alternate flow sequence similar to that explained relative to FIG. 7 but starting with a silicone vessel 110 and spin coating of the PEG-DA plus the Darocur solution and the enzyme 120 as a pre-polymeric solution that includes the vinylferrocene on the flexible substrate. It is then exposed to the ultraviolet radiation through an optical photomask 122 with the hydrogel charge acting as a negative resist. Development occurs in water to remove the membrane not exposed to ultraviolet light.

Figure 11:
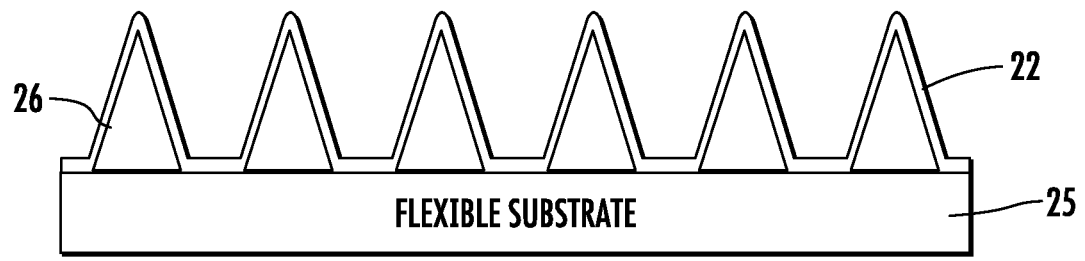
FIG. 11 is a sectional view of the microneedle array device after deposition of an electrically conductive layer before etching of the tip.
Figure 12:
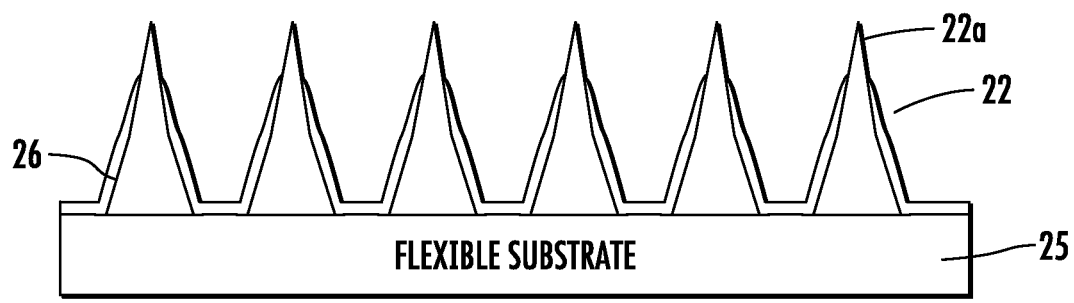
FIG. 12 is a sectional view of the microneedle array device after etching of the tip.
Figure 13:
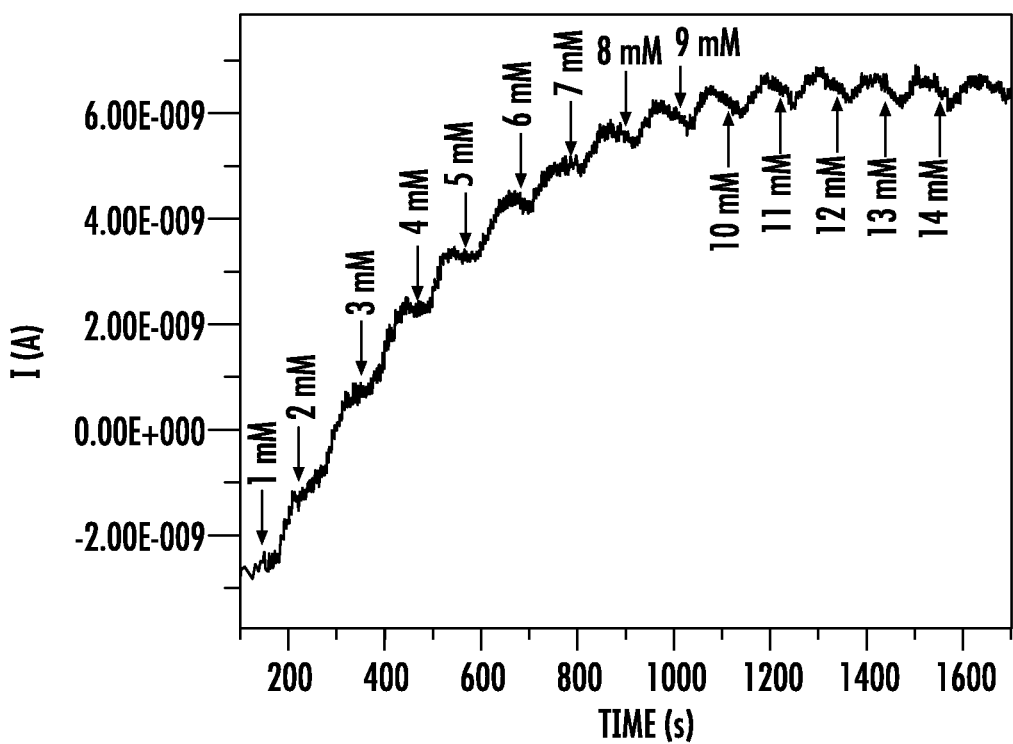
FIGS. 13 and 14 are graphs showing the response to lactate using the microneedle array device.
Figure 14:
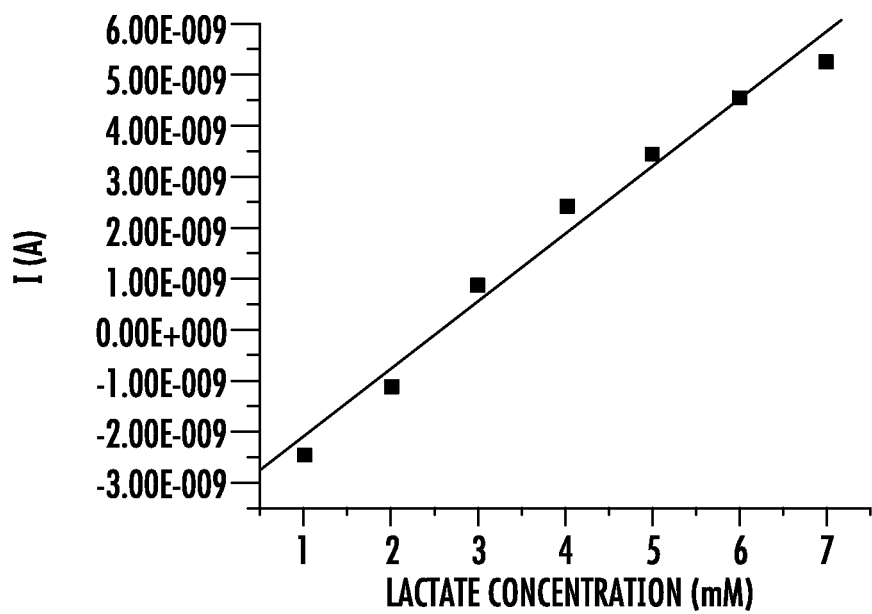

FIG. 10A shows the microneedle array on the flexible substrate 25 corresponding to the left side flow sequence of FIG. 8 while FIG. 10B shows the microneedle array on the PEG-DA hydrogel layer as shown on the right side of FIG. 8, which could then be placed on a substrate to form a patch. FIG. 11 shows the electrodes 22 on the hydrogel-based microneedle and the deposition of the conductive layer as a metal layer (Au/Ti) on the microneedle array by chemical or physical deposition. FIG. 12 shows the opening of the gold coated hydrogel-based microneedle's tips by etching of the tips of the microneedle array dipping in gold etchant solution. The rinsing in water interrupts the etching process to form the final microneedle array device to include the exposed sensing area that is formed from the hydrogel plus the redox enzyme and redox mediator. The residual part is covered by the electrically conductive layer as gold and acts as the electrode area. The microneedle array device forms a biocompatible biosensor that provides a good response to the analyte in a range of concentration consistent with human values and the sensibility at least of 1 uA/mMCM$^2$. FIGS. 13 and 14 show the response with lactate and time on the horizontal axis of FIG. 13 and the lactate concentration in FIG. 14.

It is possible to use other embodiments to form other types of configurations. For example, one configuration could include each single microneedle arranged on the top of single or multiple electrodes forming an array interconnected on the flexible substrate. Needles are the sensitive part of the device, able to record a bioanalyte concentration using PEG-DA with the photo initiator. Another configuration includes a hydrogel microneedle entirely covered by a metal layer covalantly linked to a proper enzyme. Alternatively, the metal layer is linked to a polymer that is, in turn, bonded with an enzyme. In this example, the hydrogel-based microneedle acts as a support and each single microneedle is connected with others forming an array.

Overall, the device includes the array of biocompatible hydrogel microneedles and may allow the possibility of multianalyte monitoring in the interstitial tissue with reduced pain, a minimum amount of space on the body, and a fast response. The needle-shape of each microneedle and the microelectrode array allows a greater number of sensing elements in a little space, thus improving the device response and minimizing patient compliance issues. The large number of needles arranged in a little space gives the same response that usually is provided by a larger device. All materials may be commercially available and this allows a strong cost reduction. The microneedle array is arranged in one example in a patch to provide a discrete, portable and non-invasive device for all patients. In the example shown in FIG. 3A, the flexible substrate forms a patch that is about the size slightly smaller than the tip of the index finger, as illustrated.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A microneedle array device comprising:
a substrate;
an array of microneedles on the substrate, wherein each microneedle is made of a hydrogel, the hydrogel comprising a redox enzyme and a redox mediator; and
an electrically conductive layer on the substrate, wherein the electrically conductive layer extends along a sidewall of each microneedle of the array of microneedles to a first height without covering a tip of a corresponding microneedle, the first height being between about 30% to about 90% of a height of the corresponding microneedle, wherein the electrically conductive layer does not extend into the corresponding microneedle, wherein the electrically conductive layer does not extend directly under the corresponding microneedle, and wherein the tip of the corresponding microneedle not covered with the electrically conductive layer is configured to act as a sensing area of the microneedle array device and to shuttle electrons from the redox mediator through the hydrogel to the electrically conductive layer.

2. The microneedle array device according to claim 1 wherein the substrate comprises a flexible polymeric sheet selected from the group consisting of PET (polyethylene terephthalate), PEN (polyethylene naphthalate), PEEK (polyether ether ketone), PI (polyimide), silicones, and siloxanes.

3. The microneedle array device according to claim 1 wherein each microneedle is configured to cause indentation in human body tissue, wherein the hydrogel comprises a biocompatible and photodefinable hydrogel, wherein the biocompatible and photodefinable hydrogel comprises:
a monomer, an oligomer, a prepolymer, or a combination thereof;
a binder; and
photo-active materials (PAC) or photoinitiators (PhI).

4. The microneedle array device according to claim 1 wherein each microneedle is configured to cause indentation in human body tissue, wherein the hydrogel comprises a biocompatible and photodefinable hydrogel, wherein the biocompatible and photodefinable hydrogel comprises polyethylene glycol diacrylate.

5. The microneedle array device according to claim 4 wherein the polyethylene glycol diacrylate has a molecular weight between 200 to 6,000 daltons.

6. The microneedle array device according to claim 3 wherein the biocompatible and photodefinable hydrogel comprises a material selected from the group consisting of:

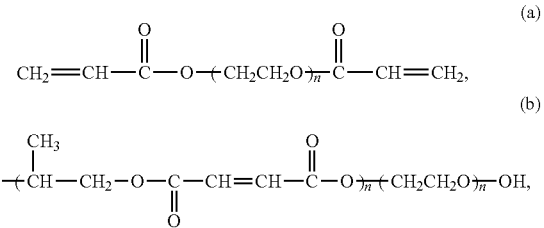

15

-continued (c)
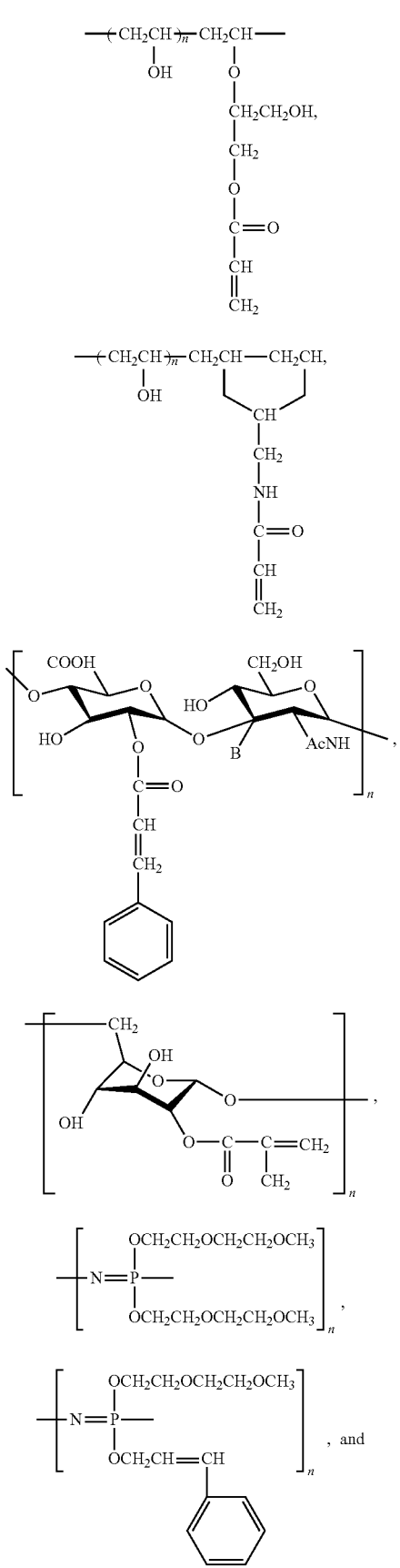
(d)
(e)
(f)
(g)
(h)

16

-continued (i)

$$\underset{PVA}{\left[\begin{array}{c}OH\\\\\end{array}\right]_n}\quad\underset{PHEMA}{\left[\begin{array}{c}O\!\!=\!\!C\!\!-\!\!O\!\!-\!\!CH_2CH_2OH\\ |\\CH_3\end{array}\right]_n}$$

wherein each of n and m is a positive integer.

7. The microneedle array device according to claim 1 wherein the redox enzyme comprises glucose oxidase or lactate oxidase.

8. The microneedle array device according to claim 1 wherein the redox mediator is selected from the group consisting of vinylferrocene, ferrocene derivatives, ferricyanide, conducting organic salts, tetrathiafulvalene-tetracyanoquinodimethane (TTF-TCNQ), quinone compounds, transition-metal complexes, and phenothiazine and phenoxazine compounds, and osmium bipyridine complexes.

9. The microneedle array device according to claim 1 wherein the redox mediator shifts between oxidized and reduced states and facilitates electron transfer during a reaction between an analyte and the redox enzyme in a physiological medium.

10. The microneedle array device according to claim 9 wherein the analyte comprises at least one of glucose or lactate.

11. The microneedle array device according to claim 1 further comprising a controller coupled to the array of microneedles.

12. The microneedle array device according to claim 1 wherein the electrically conductive layer is further configured to electrically connect each microneedle to other microneedles.

13. A microneedle array device comprising:
a flexible substrate;
an array of microneedles on the flexible substrate extending away from the flexible substrate, wherein each microneedle is made of a hydrogel, the hydrogel comprising a redox enzyme and a redox mediator; and
an electrically conductive layer on the flexible substrate and partially covering a sidewall of each microneedle of the array of microneedles and exposing a tip of a corresponding microneedle, wherein the tip of the corresponding microneedle is configured to act as a sensing area of the microneedle array device and to shuttle electrons from the redox mediator through the hydrogel to the electrically conductive layer, and wherein the electrically conductive layer does not extend directly under the corresponding microneedle.

14. The microneedle array device according to claim 13 wherein a layer formed from an organosilane solution acting as adhesive layer is interposed between the flexible substrate and the hydrogel.

15. The microneedle array device according to claim 13 wherein each microneedle is configured to cause indentation in human body tissue, the hydrogel comprises a biocompatible and photodefinable hydrogel, the biocompatible and photodefinable hydrogel comprising:
a monomer, an oligomer, a prepolymer, or a combination thereof;
a binder; and
photo-active materials (PAC) or photoinitiators (PhI).

16. The microneedle array device according to claim 13, wherein each microneedle is configured to cause indentation in human body tissue, the hydrogel comprises a biocompatible and photodefinable hydrogel, wherein the biocompatible and photodefinable hydrogel comprises polyethylene glycol diacrylate.

17. The microneedle array device according to claim 13 wherein the redox enzyme comprises at least one of glucose oxidase and lactate oxidase.

18. The microneedle array device according to claim 13 wherein the redox mediator is selected from the group consisting of vinylferrocene, ferrocene derivatives, ferricyanide, conducting organic salts comprising tetrathiafulvalene-tetracyanoquinodimethane, TTF-TCNQ, quinone compounds, transition-metal complexes, phenothiazine and phenoxazine compounds, and osmium bipyridine complexes.

19. A microneedle array device comprising:
a substrate;
an array of microneedles disposed on the substrate, wherein each microneedle is made of hydrogel, the hydrogel comprising a redox enzyme and redox mediator, wherein the redox mediator is configured to shift between oxidized and reduced states and facilitate electron transfer during a reaction between an analyte and the redox enzyme in a physiological medium; and
an electrically conductive layer on the substrate, the electrically conductive layer partially covering a sidewall of each microneedle of the array of microneedles without covering a tip of a corresponding microneedle, wherein the electrically conductive layer does not extend into the corresponding microneedle, wherein the electrically conductive layer does not extend directly under the corresponding microneedle, and wherein the tip of the corresponding microneedle not covered with the electrically conductive layer is configured to act as a sensing area of the microneedle array device and includes no cavity and to shuttle electrons from the redox mediator through the hydrogel to the electrically conductive layer.

20. The microneedle array device according to claim 19, wherein the hydrogel comprises a biocompatible and photodefinable hydrogel, the biocompatible and photodefinable hydrogel comprising:
a monomer, an oligomer, a prepolymer, or a combination thereof;
a binder; and
photo-active materials (PAC) or photoinitiators (PhI).

21. The microneedle array device according to claim 19, wherein the hydrogel comprises polyethylene glycol diacrylate.

22. The microneedle array device according to claim 19, wherein each microneedle is configured to cause indentation into a body tissue.

23. The microneedle array device according to claim 19, wherein the redox enzyme comprises at least one of glucose oxidase and lactate oxidase.

24. The microneedle array device according to claim 19, wherein the redox mediator is selected from the group consisting of vinylferrocene, ferrocene derivatives, ferricyanide, conducting organic salts comprising tetrathiafulvalene-tetracyanoquinodimethane, TTF-TCNQ, quinone compounds, transition-metal complexes, phenothiazine and phenoxazine compounds, and osmium bipyridine complexes.

* * * * *

UNITED STATES PATENT AND TRADEMARK OFFICE
CERTIFICATE OF CORRECTION

PATENT NO. : 10,987,039 B2  
APPLICATION NO. : 14/558779  
DATED : April 27, 2021  
INVENTOR(S) : Di Palma et al.

Page 1 of 2

It is certified that error appears in the above-identified patent and that said Letters Patent is hereby corrected as shown below:

In the Claims

In Column 14, Line 11, Claim 1, delete "made of a hydrogel" and insert --made of hydrogel--.

In Column 14, Lines 56-67, Claim 6, delete the equations and insert (a) 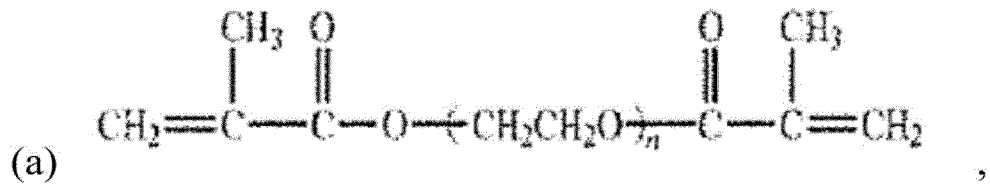 , (b) 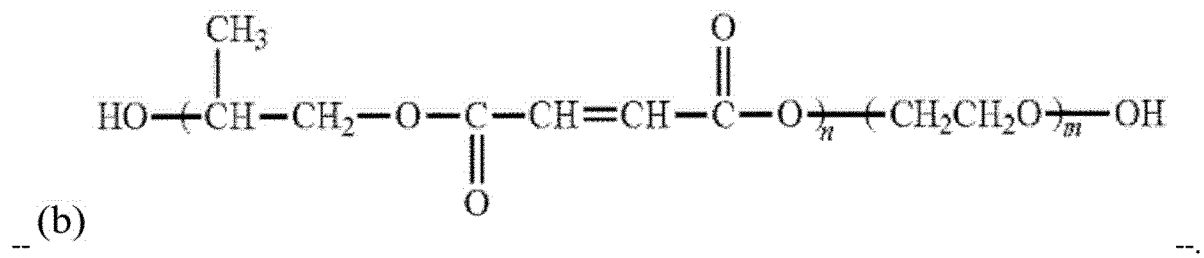 --.

Signed and Sealed this  
Twenty-fourth Day of August, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,987,039 B2

In Column 15, Lines 28-53, Claim 6, delete the equations and insert

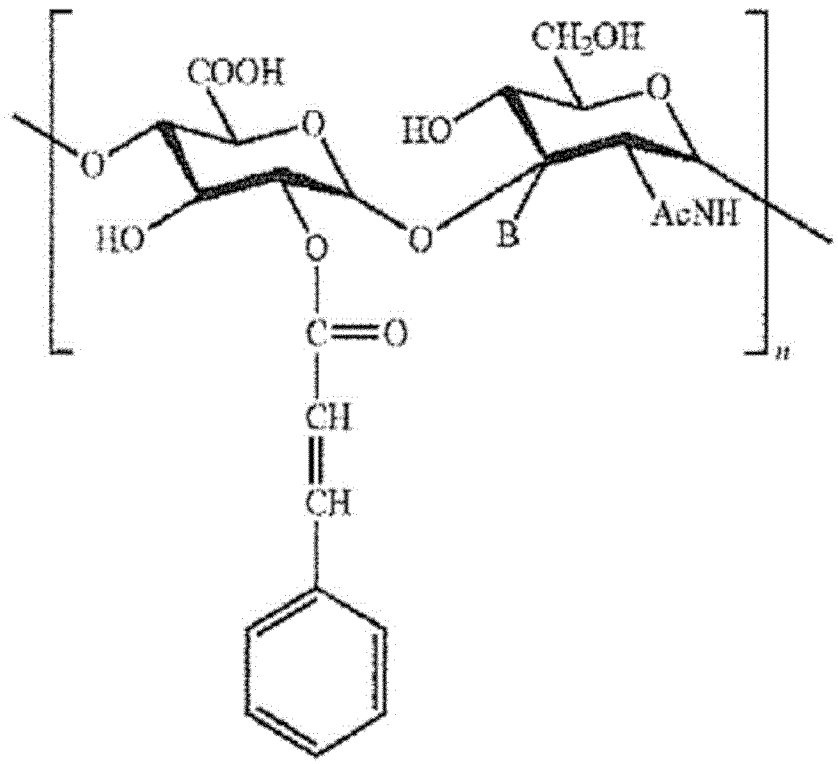

-- (e)

(f)

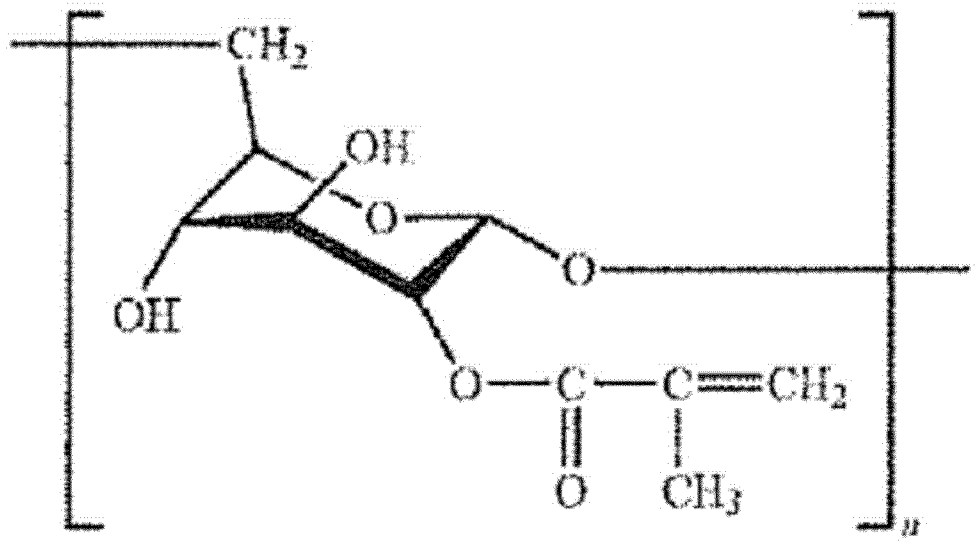

' --.

In Column 16, Line 41, Claim 13, delete "made of a hydrogel" and insert --made of hydrogel--.